United States Patent [19]

Krohn

[11] 4,155,734
[45] May 22, 1979

[54] PREPARATION OF PHOTOCHROMIC GRADIENT LENSES

[75] Inventor: David A. Krohn, Hamden, Conn.

[73] Assignee: American Optical Corporation, Southbridge, Mass.

[21] Appl. No.: 849,275

[22] Filed: Nov. 7, 1977

Related U.S. Application Data

[62] Division of Ser. No. 657,006, Feb. 10, 1976.

[51] Int. Cl.$^2$ .................. C03C 15/00; C03B 31/00; C03C 3/04
[52] U.S. Cl. ........................ 65/30 R; 65/33; 65/111; 65/115; 65/119; 65/DIG. 2; 106/52; 106/DIG. 6
[58] Field of Search ............. 65/30 R, 33, 111, 115, 65/119, DIG. 2; 106/52, DIG. 6

[56] References Cited

U.S. PATENT DOCUMENTS 4,072,490  2/1978  Illig .................... 65/30 R

Primary Examiner—S. Leon Bashore
Assistant Examiner—F. W. Miga
Attorney, Agent, or Firm—Jeremiah J. Duggan; Stephen A. Schneeberger; Alan H. Spencer

[57] ABSTRACT

Glass lenses or lens blanks, containing all the ingredients necessary to produce phototropic or photochromic behavior, are treated in a conventional production furnace to produce a locally variable heat treatment, wherein at least one portion thereof is raised to a temperature exceeding the glass strain point but not the softening point, and other portions are heated to variable temperatures decreasing from the strain point. The treatment causes development of phototropic or photochromic behavior only in those portions of the lenses or lens blanks exposed to the temperature above the strain point.

4 Claims, 7 Drawing Figures

SCHEMATIC REPRESENTATION OF APPEARANCE OF A PLANO LENS AND CORRESPONDING VISUAL TRANSMITTANCE ALONG CENTER LINE OF THE SAME LENS BEFORE A AND AFTER B EXPOSURE TO SUNLIGHT.

PREPARATION OF PHOTOCHROMIC GRADIENT LENSES

The present application is a division of application Ser. No. 657,006.

CROSS-REFERENCE TO RELATED APPLICATIONS

This invention provides improvement of the methods of manufacture of such lenses and lens blanks as fully set forth in related patent application Ser. No. 624,688, filed Oct. 22, 1975, abandoned in favor of Ser. No. 668,175 filed Mar. 19, 1976, now U.S. Pat. No. 4,036,624 issued July 19, 1977; pending application Ser. No. 789,585 filed Apr. 21, 1977, now U.S. Pat. No. 4,101,302, issued July 18, 1978, pending application Ser. No. 785,492 filed Apr. 7, 1977; and copending application Ser. No. 657,006 filed Feb. 10, 1976; all assigned to the Assignee of the present application.

This invention relates to the preparation of lenses or lens blanks having phototropic or photochromic qualities, more particularly to the preparation of such lenses or lens blanks having continuous gradations in the phototropic behavior.

BACKGROUND OF THE INVENTION

The related applications, identified above, set out fully the background of the invention and prior art of this invention. The following description briefly sets out some of the background and prior art of the invention, set out in said applications;

Ophthalmic lenses serve basically three purposes;
(1) correction of vision defects
(2) protection against mechanical hazards to the eye; and
(3) protection against radiation.

The first purpose is accomplished with transparent lenses having refractive powers, and the second purpose is accomplished by providing lenses of the required physical strength. The third purpose of protection against radiation such as ultraviolet light, intense visible light or infrared radiation can be achieved by adding color in or on the glass of the lenses or in or on the plastics or polymers of the lenses.

The colored lenses and their preparation are fully described in the above related applications.

Permanently colored or dyed ophthalmic lenses have a disadvantage of retaining low transmission of light in low levels of illumination, that is in a more or less dark environment. In such low light environments as nighttime driving, conventional sunglasses may be hazardous. It has been found that this particular disadvantage may be overcome to a certain extent, by the many varieties of phototropic or photochromic commercially available glass or plastic lenses. U.S. Pat. No. 3,197,396 describes phototropic ophthalmic lenses, containing silver ions, which are transparent to visible radiation but will darken to exposure to actinic radiation to where the transmission will be about 45% of the original transmissivity. Some of the other prior art directed to ophthalmic lenses includes U.S. Pat. Nos. 3,208,860; 3,548,060; 3,594,198; 3,617,316; 3,703,388; 3,765,913; 3,795,523; 3,833,511; 3,834,912; British Pat. No. 1,275,019; German Pat. No. 2,230,506; and German Auslegeschrift No. 2,256,775.

In addition to the above mentioned patents on photochromic glasses, all containing silver halide particles uniformly dispersed throughout the volume of an article, it is known that Chance-Pilkington Optical Glass Company, England, it marketing a phototropic phospho-silicate glass under a trade name "Reactolite."

Other photochromic glasses sensitized by silver halides are described in general in the following articles:

W. H. Armistead and S. D. Stookey: "Photochromic Silicate Glasses Sensitized by Silver Halides," SCIENCE, Vol. 144 (1964) pp. 150–154;

G. Gliemeroth and K. H. Mader: "Phototropic Glass," Angew. Chem. Internat. Edit., Vol. 9 (1970) pp. 434–445;

A. V. Dotsenko et al.: "A Study of the Effect of Copper Ions on the Relaxation Properties of Photochromic Glasses," Sov. J. P. Opt. Technol., Vol. 41 (1974) pp. 395–397;

R. J. Araujo: "Photochromic Glasses," Chapter 8 of the book PHOTOCHROMISM edited by G. H. Brown, Willey Interscience, New York (1971) pp. 667–686;

H. Bach and G. Gliemeroth: "Phase Separation in Phototropic Silver-Halide-Containing Glasses," J. Amer. Cer. Soc. (1971) pp. 43–44.

The prior art glasses seem to have in common:
1. the ingredients producing the photochromic or phototropic behavior are silver halide particles uniformly dispersed in a glass matrix; and
2. articles made from these glasses must be exposed to a well defined heat treatment to develop photochromic or phototropic behavior.

The literature described glasses appear to differ from each other in the compositions of the base glasses which serve as carriers for the phototropic or photochromic centers. U.S. Pat. No. 3,208,860 describes a phototropic article comprising a silicate glass body having in at least a portion thereof microcrystals of at least one silver halide selected from the group consisting of silver chloride, silver bromide, and silver iodide, with the concentration of said crystals in the portion being at least 0.005% by volume.

U.S. Pat. No. 3,419,370 teaches a preparation of photochromic lenses by diffusing silver ions into the surface layer of a base glass and then exposing the articles to a specific heat treatment. Glass or plastic articles have also been prepared as photochromic materials by coating the substrates with a phototropic coating as described in U.S. Pat. No. 3,875,321 and described in The Journal of the American Ceramic Society (1974) pps. 332–335 under the title "Reversible Optical Density Changes in Composite Layers."

The photochromic or phototropic lenses above described have certain advantages over permanently tinted lenses. Thus because of the reversibility of the photochromic effect such lenses assume a low transmissivity if exposed to ultraviolet or blue light but resume high transmissivity in an environment where low illumination levels of activating radiation prevail. Glass lenses do not appear to lose photochromic properties as do plastic phototropic lenses during extended wear causing degradation of active ingredients.

All presently known photochromic or phototropic lenses have the disadvantage that recovery of high transmissivity takes several minutes. This has been noticed with discomfort and dislike by wearers under such conditions as driving an automobile where low levels of illumination exist inside the car and high levels of illumination may exist outside the vehicle. While it is desirable to reduce the light intensity to the driver's eyes while observing road and traffic conditions, the driver must be permitted to clearly view information presented by instruments on the vehicle instrument panel where a low level of illumination normally exists. Indeed, it may be dangerous to prevent this. A similar type of problem may be found in occupations where sudden changes in the level of illumination from bright to dim occur either (1) by rapid changes in the intensity of the light source or (2) by movement of the wearer of the spectacles from high level of intensity to a darker environment.

Some of the disadvantages have been overcome by the use of eyeglasses with a continuous variation of transmissivity from low at the top of the lens to high over the lower portion of the lens. Lenses with such a permanent gradient in degree of color or tint are now available in commerce, and it is believed that such lenses are prepared by differentially dyeing plastic lenses or by applying a graded color coating over glass lenses by vacuum deposition of absorbing materials. With plastic lenses such color gradient may be achieved by concentration of the dye absorbed by the lens by different areas. For example, a high concentration of absorption prevails at the top and a low concentration at the bottom of the lens.

In U.S. Pat. No. 3,419,370 there is found a statement that a gradient in photochromic behavior across a glass body is attainable by varying the time and/or temperature at different portions of the glass body exposed to an ion exchange medium. According to this patent the ion exchange bath contains, in all instances, silver ions (see Table 2 of the patent). The gradient in photochromic properties is achieved by causing or allowing different concentrations of silver ions to diffuse into the glass. The teachings of the patent, in our opinion, is that glass cannot be made photochromic or phototropic without having been exposed to the diffusion process in the silver containing ion exchange bath prior to the heat treatment required to develop phototropic or photochromic behavior. The base composition of the glasses do not contain any silver ions, nor is there a teaching of a photochromic gradient over ophthalmic lenses.

In our opinion, the state of the art of making ophthalmic lenses uniformly phototropic or photochromic throughout their entire volume can be summarized as follows:

1. Glasses of the types listed in Table 1 hereafter are melted following procedures known to those skilled in the art of glass making.
2. Lens blanks are made of these glasses by known methods such as pressing or casting.
3. These articles are exposed to a controlled heat treatment to develop silver halide particles of linear dimensions d falling essentially within the range $5 < d < 50$ nm. The lower limit is required to produce photochromic or phototropic behavior, the upper limit to avoid light scattering unacceptable in ophthalmic products. The total concentration of these silver halide particles which are dispersed uniformly throughout the glass article should be at least 0.005 vol. %.

In our opinion, the state of the art of making glass articles with a gradient in photochromic or phototropic behavior as deduced from U.S. Pat. No. 3,419,370 can be summarized as follows:

1. A base glass having a composition in essence in the general system Alk. Oxide—$Al_2O_3$—$B_2O_3$—$SiO_2$, with addition of halides to the batch, is melted under conditions that allow retention of a sufficient quantity of halides.
2. Lens blanks are made from the glasses by known methods such as pressing or casting.
3. Finished lenses are made from the blanks by grinding and polishing.
4. The finished lenses are exposed to a source of silver ions at elevated temperature in such a fashion that in those parts of the lens where a high degree of phototropic or photochromic behavior is desired the silver concentration is higher than in those parts where a low degree of phototropic or photochromic behavior is desired.
5. The thus treated lenses are exposed to a carefully controlled heat treatment to grow silver halide crystals to a size required for photochromic or phototropic behavior, but not exceeding linear dimensions of 50 nm to avoid the light scattering unacceptable in ophthalmic lenses.

SUMMARY OF THE INVENTION

Ophthalmic lens pressings which do not exhibit phototropic or photochromic behavior are made from glasses containing all necessary ingredients to produce such phototropic or photochromic behavior. Such glass is hereafter sometimes referred to as "unnucleated" photochromic glass. This expression is used herein for reasons of simplicity. As clearly pointed out in the related applications, the submicroscopic nuclei required to develop silver halide particles exist in the non-phototropic state of the glass. In other words, the nuclei are so small they cannot be seen with a light microscope since they do not apparently reflect light. Numerically speaking, they have a maximum linear dimension which is less than about 5 nm. As will be recognized by one skilled in the art, these particles are too small to interact with light in the visible spectrum. While the nuclei has not been actually measured, the 5 nm number is chosen as having meaning to one in this art. The pressings are not exposed to the heat treatment required to develop photochromic or phototropic behavior. The pressings are transferred or made into lens blanks, the blanks are given a gradient in their phototropic or photochromic behavior by exposing them to a temperature gradient field. The exposure is such that one portion of the blank is heated to a temperature to above the strain point but below the temperature of the softening point of the glass, while a distance part of the blank is maintained at a temperature below the strain point.

It has also been found that ophthalmic lenses made from unnucleated glass pressings which have been exposed to the specific heat treatment required to develop photochromic or phototropic behavior, can be made into semi-finished or finished lenses having their gradient in their phototropic or photochromic behavior across the face of the lens.

It has been found that so-called "one-piece multifocal" or "raised ledge multifocal" glass lenses and progressive power glass lenses with desirable properties can be made with a gradient in the phototropic or photochromic behavior since such lens designs are particularly suited to the practice of the present invention. The portion of the lens used for distant vision can be made phototropic or photochromic whereas the portion of the lens used for near vision will not have such properties. To achieve such a gradient in photochromic or phototropic behavior, raised ledge multifocal lenses or lens blanks suitable for subsequent generating and polishing are exposed to a temperature gradient as described below, alternatively, finished lenses may be exposed to a corresponding temperature gradient.

The present invention is applicable to glass lens blanks and lenses which contain all of the ingredients required for producing photochromic or phototropic behavior substantially uniformly dispersed throughout the glass body but having silver halide in an unnucleated state, i.e., particles of less size than that required to produce photochromic or phototropic behavior. It is preferred to use glasses with a coefficient of expansion below $60 \times 10^{-7}$ per degree C. to reduce thermal fracture of lenses and blanks during treatment in the temperature gradient field. However, the invention is not limited to such glasses. The invention contemplates the thermal masking of the lens blank so as to suppress the development of photochromic behavior in the masked portion whereby a progressive gradient photochromic behavior with a continuously varying transmissivity is produced therein.

DESCRIPTION OF THE PREFERRED EMBODIMENT

To better understand the processes according to the instant invention, the above related applications contain a full description of the transmission of lenses, generally as follows.

The transmission T of a glass lens can be described by the expression $$T = \exp(-K \cdot Z_o)$$

where
K—coefficient of extinction and
$Z_o$—thickness of the lens at the location of measurement measured parallel to the direction of the incident beam of light.

K is a function of the wavelength of light and for a given wavelength is normally a material constant characteristic for the glass the lens is made of. The lens thickness $Z_o$ is a variable of the two space coordinates x and y in a plane normal to the optical axis of the lens. The degree of variation of $Z_o$ depends on the Rx values of the lens. For negative lenses $Z_o$ is larger at the edge than at the center, for positive lenses $Z_o$ is larger at the center than at the edge. This results in a local variation of the light transmission T. Strong negative lenses, e.g., made of a colored glass appear to be darker at the edge than at the center. The degree of variation of T in this case is entirely determined by the shape of the lens required to achieve a specific prescription. In general, $Z_o = Z_o(x,y)$.

In case of a photochromic or phototropic lens the extinction coefficient K is time dependent and dependent upon wavelength and intensity of the activating radiation. For reasons of simplicity a monochromatic activating radiation of constant intensity shall be assumed. If t is the duration of exposure to such activating radiation $K_1$ increases with t or $$dK_1/dt < 0,$$

whereby $K_1(t)$ reaches a constant value after approximately ½ hour depending upon the glass studied and the precision of the measurement.
Therefore eq. (1) becomes $$T_1(t) = e^{-K_1(t) \cdot Z_o}$$

with $$(dT_1/dt) - Z \cdot (dK_1/dt) \cdot e^{-K_1(t) \cdot Z_o} < 0$$

i.e., the transmission decreases with increasing exposure time. The saturation value of $T_1(t)$ reached after approximately 30 minutes can be between 30 and 45% depending upon the nature of the glass and the thickness of the lens. The original transmission before exposing the lens to activating radiation is normally about 90%.

After removing the activating radiation the lens gradually regains its original transmission value. This process can be described by introducing a second time dependent extinction coefficient $K_2(t)$ with $$dK_2/dt < 0.$$

Correspondingly the change in transmission $T_2$ with time t is
$$dT_2/dt = Z_o \cdot |dK_2/dt| \cdot e^{-K_2(t) \cdot Z_o} > 0.$$

In general terms the transmission T of a photochromic lens therefore can be described by $$T(t, x, y) = \exp(-K_i(t) \cdot Z_o(x,y))$$

with $K_i(t) = K_1(t)$ during exposure to activating radiation,
and
$K_i(t) = K_2(t)$ after removing the activating radiation;
$Z_o$ (x, y) is determined by the prescription values required to provide for correction of vision in each individual case.

To achieve a gradient in phototropic or photochromic behavior across the face of a lens the coefficient of extinction K must be a function of the two space coordinates x and y in addition to its dependence of time:

$$K = K(t, x, y).$$

The corresponding expression for light transmission through the lens at a point x,y is $$T(t, x, y) = \exp(-K(t, x, y) \cdot Z_o(x,y)).$$

which for plano lenses can be simplified to $$T(t, x, y) = \exp(-K(t, x, y) \cdot Z_o)$$

with $Z_o$ = constant.

To achieve such a space dependent coefficient of extinction prior art U.S. Pat. No. 3,419,370 teaches utilization of a corresponding variation in the concentration of silver required to form silver halide crystals providing for phototropic or photochromic behavior. As indicated above in the section "Background Discussion of the Prior Art" such a process is only applicable to finished lenses. It is furthermore very difficult to control and requires an additional step; namely, the introduction of silver ions through a diffusion process. It furthermore requires use of a glass melted under special conditions to retain sufficient halogen to form silver halide particles.

Prior workers have failed to recognize or appreciate that all potentially phototropic or photochromic glass articles utilizing silver halide particles to achieve phototropic or photochromic behavior can be used to prepare articles with a gradient in that behavior. To produce an extinction coefficient K (t, x, y) through local variation of the silver concentration the prior workers have used a specially melted glass and subsequent exposure to a silver diffusion process. In contrast we provide a locally variable extinction coefficient through well controlled development of a proper size distribution of silver halide particles in unnucleated glass initially containing all of the necessary silver and halogen atoms uniformly distributed throughout the entire volume of the glass article. Such a desirable size distribution of silver halide particles is achieved by carefully controlled exposure to a locally variable temperature field. This can be done with either lens blanks or finished lenses. Such lenses are made of glass which can be described as "potentially photochromic or phototropic glass."

While practicing the present invention, care must be taken to avoid thermal fracture of the lenses or lens blanks when they are exposed to a locally variable temperature field. Glasses with a low coefficient of thermal expansion, such as certain borosilicates, are better suited for this application than glasses with a high coefficient of thermal expansion such as the phosphosilicates. Boro-silicate glasses have coefficients of thermal expansion in the range approximately 30 to $60 \times 10^{-7}/°$ C. To the best of our knowledge other glasses used commercially as a carrier of matrix for phototropic or photochromic centers have coefficients of thermal expansion of $90 \times 10^{-7}/°$ C. and above. The higher the coefficient of thermal expansion, the higher the thermal stresses existing in the glass article when they are exposed to a temperature gradient.

BRIEF DESCRIPTION OF THE DRAWINGS

In one example of a process of the invention shown in FIGS. 1 and 2 a disk-like glass pressing or lens blank 10, consisting of an unnucleated photochromic glass having a thickness of 8.5 mm and a diameter of 65 mm, was mounted on a ceramic block 12. A 9-inch straight brick 14 consisting of a Johns-Manville Company insulated brick, identified as "J-M 23" was cut out along lines 16 to encapsulate a portion of the lens and ceramic block assembly by having the brick portions a close distance from the lens blank. The combination of the lens 10 and support ceramic block 12 in the space in the insulated brick were placed in a regular laboratory electric furnace which is operated normally, that is in the ambient atmosphere with no special atmosphere or the like. The furnace was raised to a temperature of about 1240° F. and was maintained at that temperature for about 20 to 30 minutes. The insulated brick masked a portion of the glass so that it did not attain the temperature of the furnace. The furnace then was allowed to return to room temperature, about 70° F. The lens was then recovered and tested. The lens showed the desirable variable photochromicity. The glass of the lens may be made of one of the compositions such as shown in Table 1. In FIGS. 1 and 2 the distance between a lens 10 and the brick surface defined by the line 16 is exaggerated to better illustrate the invention. As can be seen in FIG. 2, the surface 16 should closely approximate and be the mirror image of the volume field between lens 10 and the block 12.

Table 1

| Compositions in wt % of Unnucleated Glasses Useable According to This Invention | | | | | |
|---|---|---|---|---|---|
| | A | B | C | D | E |
| $SiO_2$ | 53.0 | 21.4 | 58.8 | 57.3 | 0.0 |
| $Al_2O_3$ | 10.5 | 37.7 | 22.9 | 9.1 | 8.3 |
| $ZrO_2$ | 2.0 | 0.0 | 0.0 | 0.0 | 1.3 |
| $Li_2O$ | 2.1 | 0.0 | 4.5 | 0.0 | 0.0 |
| BaO | 6.0 | 5.5 | 0.0 | 0.0 | 3.3 |
| SrO | 0.2 | 0.0 | 0.0 | 0.0 | 0.0 |
| $Na_2O$ | 0.6 | 3.8 | 1.5 | 6.5 | 16.2 |
| NaF | 1.0 | 1.0 | 4.7 | 3.1 | 0.0 |
| NaCl | 1.0 | 1.0 | 1.8 | 2.6 | 1.0 |
| $Ag_2O$ | 0.4 | 0.5 | 0.4 | 0.5 | 0.6 |
| PbO | 5.1 | 0.0 | 0.0 | 1.0 | 0.0 |
| CuO | 0.1 | 0.1 | 0.02 | 0.02 | 0.02 |
| $P_2O_5$ | 0.0 | 15.6 | 0.0 | 0.0 | 7.5 |
| $B_2O_3$ | 18.0 | 4.8 | 2.5 | 18.6 | 61.8 |
| $K_2O$ | 0.0 | 8.6 | 0.0 | 0.0 | 0.0 |
| NaBr | 0.0 | 0.0 | 0.8 | 1.3 | 0.0 |
| MgO | 0.0 | 0.0 | 2.1 | 0.0 | 0.0 |

Colorants well known to those skilled in the art may be included. Such colorants are substantially neutral or non-reactive as far as the other glass constituents are concerned. Exemplary ones include: transition metal oxides including such as $Fe_2O_3$, $Cr_2O_3$, CoO; certain rare earth oxides such as $Nd_2O_3$, $Pr_2O_3$.

Figure 1:
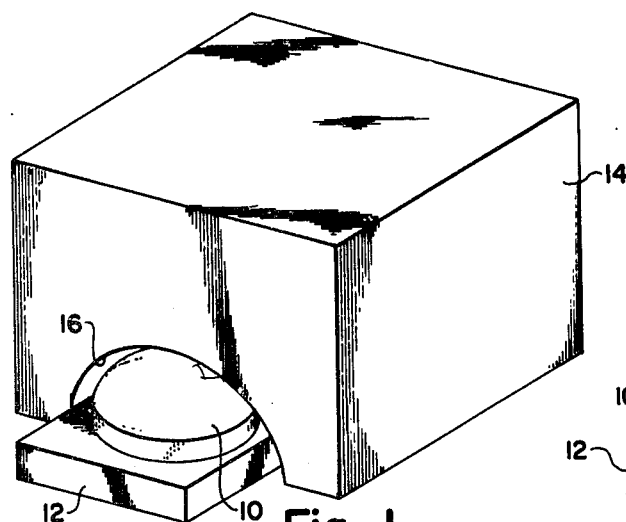
FIG. 1 is a schematic, perspective view of one form of partial masking means for portions of lens blanks or lenses for heating to a temperature gradient required for producing lenses or lens blanks according to the invention.
Figure 2:
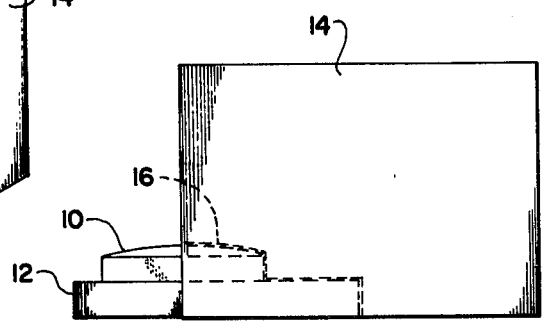
FIG. 2 is a side elevational view of the device of FIG. 1.
Figure 3:
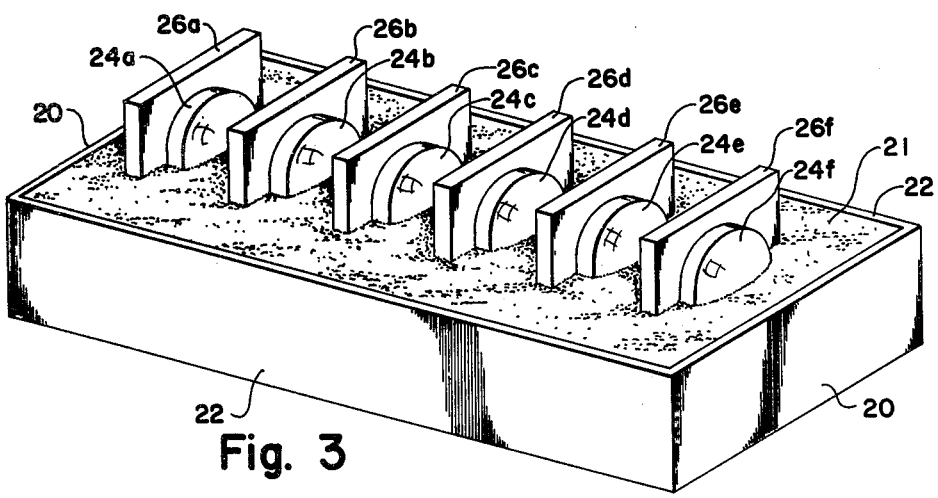
FIG. 3 is a perspective view of a modified form of an arrangement for the variated heating of a plurality of lenses or lens blanks.
Figure 5:
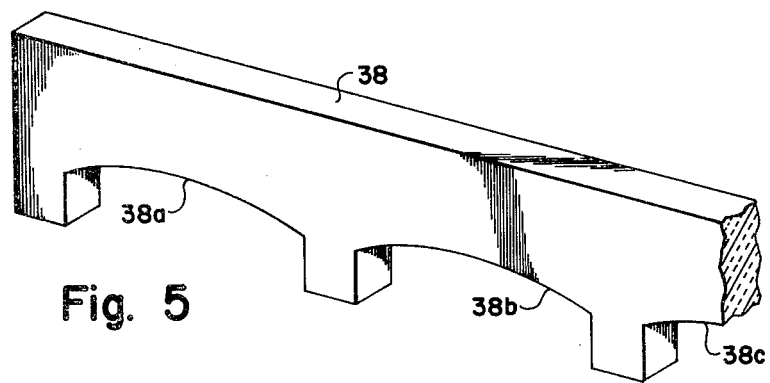
FIG. 5 is a partial perspective view of element 38 of FIG. 4.

In a second example, FIG. 3, a plurality of lenses are placed in a stainless steel fusion tray containing conventional glass makers silica of conventional sizing, to a depth of about 1¾ inches. The tray, shown in FIG. 3, includes ends 20 and sides 22 connected to a bottom not shown. The conventional stainless steel fusion tray is approximately 12 inches long, 6 inches wide, and 2½ inches high. Spaced at substantially equal distance intervals along the length of the tray are a series of lenses 24a through 24f, each frictionally supported on a conventional chromite fusing block 26a through 26f respectively. The lenses on the blocks are inserted in the sand 21 at a slight angle. The frictional engagement is descriptive of the actual relationship that is not crucial to the assembly. In actual commercial production, suitable stops and guages accurately and reproducibly control the depth and positioning of the lenses and the blocks in the sand 21. The fusing tray with the lenses or lens blanks positioned in the sand is then placed in conventional equipment as used by Americal Optical Corporation, assignee of this application, for the commercial manufacture of ordinary photochromic bifocal lenses. Such equipment is adequately described in the application Ser. No. 624,688. As will be recognized by those skilled in the art, other conventional equipment of this type may be used.

As it is well known to those skilled in the art, conventional glass makers silica is relatively coarse and of a very high purity. Most important, the iron content to avoid contamination of the lens blanks must be less than 200 parts per million.

Figure 6:
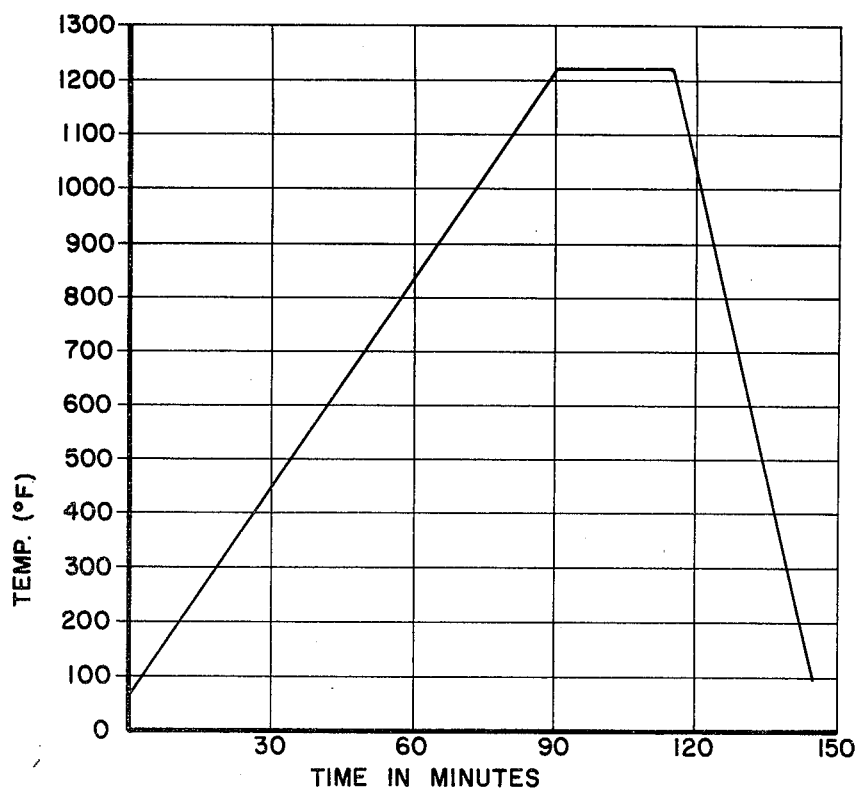
FIG. 6 is a general temperature profile for the time-temperature relationship for producing variable heating of lens portions according to the invention.

The tray with the silica and the mounted lenses and blocks is placed in a conventional production photochromic bifocal furnace, and the temperature is raised to about 1220° F. over a period of ninety minutes. Once the 1220° F. temperature is reached, the assembly with the lenses is permitted to soak at that temperature for about 20 minutes. The lenses are thereafter cooled over a period of about 30 minutes to a temperature where they can be handled, that is about 100° F. The time-temperature profile is shown in FIG. 6.

The lenses treated according to the method just described provided lenses which were in all respects fully equivalent to lenses produced according to related applications described above and equivalent to the first example described herein.

Figure 4:
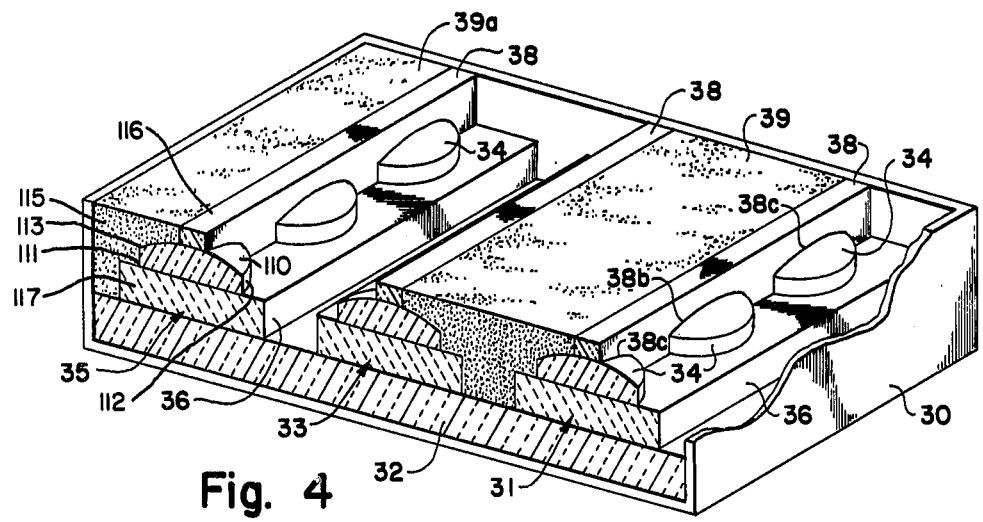
FIG. 4 is a cut-away perspective view of a further modified method for the variated temperature treatment of a plurality of lenses or lens blanks.

In a third example, illustrated in FIG. 4, a stainless steel fusing tray 30, of the same dimensions as given above, has its inside bottom covered with a 1 inch asbestos sheet 32. A series of lenses 34, each mounted on a chromite fusing block 36, are positioned on the asbestos. A strip of asbestos 38 is mounted on each lens or series of lenses in such a manner that the strip 38 forms a dam at about the middle of the lenses. Thus, this strip 38 includes cutouts 38a, 38b and 38c which conform closely to the curvature of the lens blanks so as to rest on the surface of the lens blanks. Between the series of lenses 31 and the series 33 and their positioned or overlying asbestos strip 38 is a bed of coarse glass makers silica of the type described above, and of a sufficient depth to blanket that portion of each of the lenses which is to be heated to a temperature below the strain point, described in the related applications. A second bed of sand 39a is formed between a wall of the tray and the dam 38 in the series 35. Thus, about half of each lens in each series will be exposed to full temperature of the atmosphere of the oven, while a lens under the sand is raised to a lesser temperature. With the lenses, dams, and masking silica mounted in the tray, the tray is passed through a conventional production furnace, providing heating as described above.

The masking or insulating material, shown as the coarse grain, glass-makers silica may contain moisture in the form of water. It should be understood, that the sand in the embodiments where the sand is used as a masking material, functions as a heat sink. Moisture in the sand enhances the heat sink characteristics of the sand, since the water must be evaporated to permit the sand to heat much above the boiling point of water. Therefore, the quantity of water to be heated provides a degree of control of the temperature to which insulated or masked portions of each lens is to be subjected. Clearly, the more moisture in the sand, the more heat that is required to vaporize it and thus less heat is transmitted to the lenses. Further, other vaporizable liquids and solids, chemically compatible with the system may be used, for example, petroleum products including various derivative products, waxes, and other high temperature materials may be used. Furhter, metal particles may be mixed with the sand grains which form the insulated cover to enhance the heat sink characteristics thereof. Refractory grains, other than silica may be used, for example, alumina, chromite, magnesia, calcia, etc. Proper control of size gradation of the grain bed is desirable to assure all voids are filled to the highest practical extent. As will be recognized by those skilled in the refractory art, maximum packing through proper size gradation tends to eliminate trapped air.

In the foregoing, the silver halide particles are mentioned in linear dimensions. It is understood, however, that in discussing particles being smaller than about 5 nm, and which substantially progressively increase in size to about 50 nm, we are describing an average particle. An "average particle" is defined to mean a substantial preponderance of the particles have the specific linear dimensions. Obviously, some particles will be smaller and some will be larger in any given area because of the lack of precise control of the chemical reactions which result in particle formation. Further, while the photochromic material is described in silver chloride, silver bromide, and silver iodide, the silver composition may also be mixture of the same.

The glasses specified by the letters A, B, C, D and E of Table 1, may be used to practice the invention. To use the glasses, the lens or lens blanks are prepared. The strain point and the softening point of respective glasses are noted and the furnace is operated to permit an appropriate temperature above the strain point but below the softening point. The masking provides an appropriate temperature gradient along the lens. The appropriate temperature gradient permits a potential upper portion of the lens to have well-developed silver halide crystals, with a controlled progression to substantial freedom from nucleation at the bottom or potential bottom of the lenses or lens blanks. There is thus established a graded thermal masking of the lenses, or lens blanks. The maximum masking is over that area which is to serve as the reading, or bottom, portion of the lens, or lens blank, when it is glazed in a frame. There is substantially no masking over that area which is to serve as the distance portion and thus there is thermally introduced maximum nucleation. As mentioned above, the sand bath 21 serves as a heat sink thereby assisting in providing the progressive thermal gradient. This method is accomplished, of course, by assuring that the leading edge of a lens is heated about its strain point but below its softening point, while the masked portion is heated to a lower temperature. After heating, the lenses are permitted to sufficiently cool to avoid thermal fraction by conventional procedures. Further, conventional grinding, polishing, generating, edging and glazing techniques may be used to prepare and mount the lenses in frames. Suitable conventional strengthening techniques, pursuant to commercial practices, may be used to satisfy government regulations.

Figure 7:
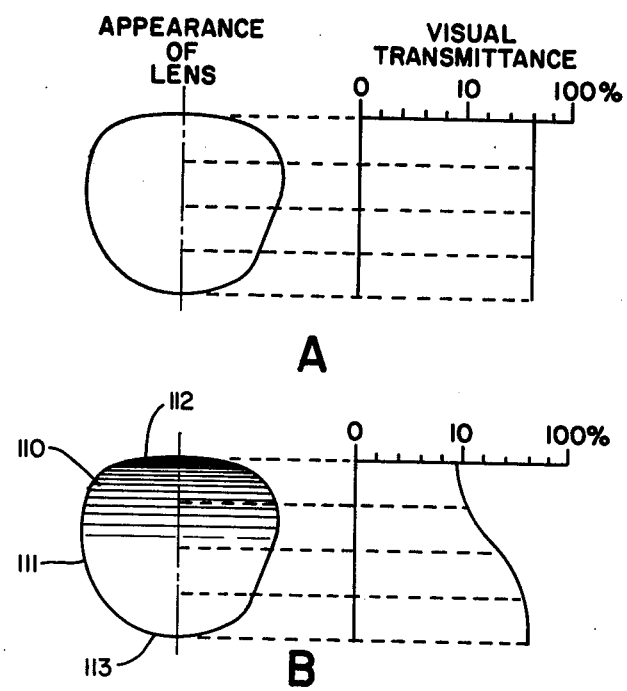
FIG. 7 is a schematic representation of the appearance of a plano lens and the corresponding visual transmittance across the face of such a lens before (a) and after (b) exposure to activating radiation (sunlight) for approximately 30 minutes.

As shown in FIG. 7, section A demonstrates transmittance of a plano lens when in its unactivated condition. Section B illustrates the gradient of transmittance of the lens after it has been exposed to sunlight for a period of time. This schematically shows the results of the lens or lens blank treatment according to the invention.

Broadly speaking, an article fabricated according to the present invention is a lens or lens blank exhibiting regressive variation in photochromic behavior from top to bottom as the lens appears in a frame. Distributed throughout the oxide glass body from which the lens or blank is fabricated are silver halide particles consisting of about at least 0.005 vol. % thereof. The silver halide particles in the finished lens are of such a size distribution that in at least one portion of the article the linear dimension of the particles are smaller than about 5 nms and their remaining portion of the article range between